United States Patent [19]

Dosoretz et al.

[11] Patent Number: 4,629,333

[45] Date of Patent: Dec. 16, 1986

[54] CHILLED MIRROR HYGROMETER WITH PERFORMANCE MONITORING

[75] Inventors: Victor J. Dosoretz, Waban; Stanley Ronchinsky, Newton Center, both of Mass.

[73] Assignee: EG&G, Inc., Waltham, Mass.

[21] Appl. No.: 663,002

[22] Filed: Oct. 19, 1984

[51] Int. Cl.$^4$ .......................................... G01N 25/02
[52] U.S. Cl. ...................................... 374/20; 374/45
[58] Field of Search ..................... 374/20, 18, 19, 17, 374/16, 45; 356/448, 446; 73/336.5

[56] References Cited

U.S. PATENT DOCUMENTS

| | | | |
|---|---|---|---|
| 3,112,648 | 12/1963 | Dulk | 374/20 |
| 3,623,356 | 11/1971 | Bisberg | 374/20 |

FOREIGN PATENT DOCUMENTS 0053992  6/1982  European Pat. Off. ............ 356/446

Primary Examiner—Charles Frankfort
Assistant Examiner—Denis E. Corr
Attorney, Agent, or Firm—Robert P. Cogan

[57] ABSTRACT

A radiation source directs light at a mirror which reflects to a first photosensor. As a dew point is reached, scattered light is reflected to a second photosensor to indicate dew point. Rather than periodically interrupting operation to test reflectivity of the mirror or to perform a heating cycle, operation is monitored continuously. The common mode output of both the first and second photosensors is monitored. When below a threshold level, the output indicates the need for cleaning the mirror. It may also be used in a closed loop to increase light source intensity as mirror reflectivity decreases.

6 Claims, 1 Drawing Figure

CHILLED MIRROR HYGROMETER WITH PERFORMANCE MONITORING

BACKGROUND OF THE INVENTION

The present invention relates to hygrometers, more specifically to chilled mirror hygrometers.

Many methods of humidity determination are based upon inferring the moisture content of a sample from an output of a moisture sensitive transducer. Such secondary methods may be subject to such inherent limitations as a non-linear variation of the output parameter with humidity, drift, temperature sensitivity, hysteresis and aging. The limitation of temperature, of course, relates to the fact that water holding capacity of a gas varies with temperature so that only a relative humitidy rather than an absolute measurement is provided. Relative humidity is related to absolute humidity by the Goff-Gratch equation, which is not conveniently embodied in a linear circuit.

Optical chilled mirror hygrometers are preferable since they provide an indication of dew point or frost point, each of which is a primary measurement of moisture content.

The dew point is the temperature at which the partial pressure of a condensate on a surface equals the water vapor partial pressure in a gas. Similarly, frost point is the saturation temperature to which the gas temperature must be cooled at constant pressure so that it will be saturated with respect to ice. Saturation vapor pressure is a unique function of temperature. Therefore, determining the temperature at which water vapor begins to condense on a cool surface is equivalent to a measurement of its partial pressure.

Optical chilled mirror hygrometers use cooled mirrors as the surface where condensation takes place. Utilizing electrooptic circuitry, a precise determination of the formation of either dew or frost is made. A temperature transducer, for example a platinum resistance transducer, is used to provide the signal indicating the output information.

In the past, a limitation of optical chilled mirror hygrometers has been the inability to differentiate between dew or frost and dirt deposits since both will be measured by a photosensor as a loss of reflected light. A prior art response has been to establish a mode of utilization of such hygrometers in which a cleaning procedure is performed periodically or on an event-dependent basis, e.g. such as at the beginning of a day's operation. Another compensating procedure is the "balancing" of a system. This is done by in essence performing a calibration operation to "null" variations in the optic sensing scheme due to dirt deposits on the mirror surface. A balancing operation calls for heating of a mirror to a temperature higher than the dew point to insure a dry mirror so that loss in reflectivity due to dirt alone may be measured. Adjustment of optical sensing circuitry must be made to compensate for any differences to respect to original calibration values.

In both situations, cleaning or calibration must be performed more often than would be called for due to any deterioration in performance so that such deterioration in performance, which would be otherwise undetected, can be avoided. Furthermore, balancing or cleaning operations necessarily require losing the ability to monitor while the operations are being performed. The operations are performed without reference to the performance of the instrument. No way is provided apart from the actual cleaning or balancing operations to increase the time between which "down" periods of the hygrometer must occur.

SUMMARY OF THE INVENTION

It is therefore an object of the present invention to provide an optical chilled mirror hygrometer in which reflectivity of a mirror can be monitored without the need for interrupting operation of the hygrometer.

It is also an object of the present invention to provide a chilled mirror hygrometer of the type described in which a measurement may be provided indicating the need for a cleaning or balancing operation, whereby such operations are performed in response to system performance and down time is minimized.

It is also a further object of the present invention to provide an optical chilled mirror hygrometer of the type described in which compensation may be provided for loss in reflectivity of the mirror, further minimizing down time of the system.

Briefly stated, in accordance with the present invention, there is provided in a chilled mirror hygrometer a light source directing radiation to a mirror, the reflection from which is measured by a first photosensor. A second photosensor is provided responsive to scattered radiation from the mirror as a function of the formation of condensation thereon. A common mode output of both the first and second photosensors is measured to provide an output indicative of reflectivity of the mirror. An output indicative of performance of the system in terms of reflectivity is thus provided. This output may be further utilized in comparison to a preselected threshold level to indicate the need for a mirror cleaning cycle or to initiate an automatic heating and cooling cycle in which reflectivity-reducing matter may be removed with condensation. Additionally, in a further embodiment, the common mode output may be used to provide for closed loop control of intensity of the radiation source. Consequently, loss in reflectivity can be compensated for, within practical limits, by increase in source intensity. The required frequency of cleaning is thereby further reduced.

BRIEF DESCRIPTION OF THE DRAWINGS

The means by which the foregoing objects and features of novelty are achieved are pointed out in the claims forming the concluding portion of the specification. The invention, both as to its organization and manner of operation may be further understood by reference to the following description taken in connection with the FIGURE.

The FIGURE is an illustration of a system constructed in accordance with the present invention;

DESCRIPTION OF THE PREFERRED EMBODIMENTS

Figure 1:
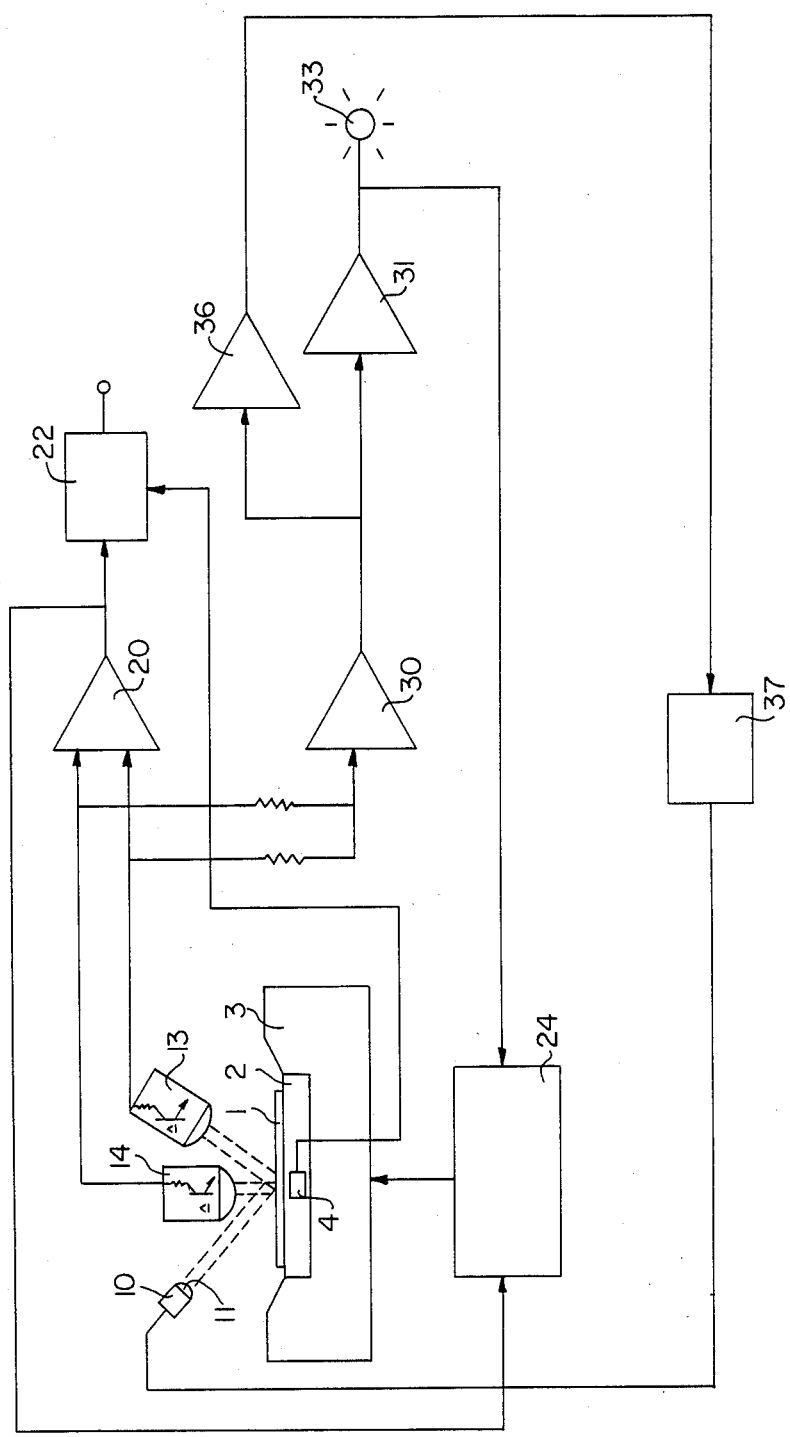

Referring now to the FIGURE, there is illustrated a chilled mirror hygrometer system constructed in accordance with the present invention. A mirror 1 is mounted on a temperature-controlled surface 2 forming a portion of a thermoelectric cooler 3 such as a Peltier effect device. temperature is measured by a thermoelectric device 4.

A radiation source 10 preferably comprises an infrared, or other light-emitting diode 11 directed at the mirror 1. The radiation source 10 could comprise a plurality of devices in separate locations. A first photodetector 13 is positioned to received refleted radiation emitted by the light-emitting diode 11 and reflected by the mirror 1. A second photodetector 14 is positioned whereas not to receive this reflected radiation. However, the photodetector 14 will receive scattered radition in response to formation of condensation on the mirror 1. Either photodetector 13 or 14 could comprise a plurality of photosensors. Within that plurality it is possible to use separate photosensors to indicate dew point and to measure total reflectivity.

The photodetectors 13 and 14 have their outputs connected to a differential amplifier 20 in a prior art manner. When there is no condensation (or dirt) on the mirror 1, the photodetector 13 will provide an output indicative of the radiation emitted by the source 10 and the photo detector 14 will produce essentially a zero level output. Of course, the photodetector 14 may receive background radiation. However, it is contemplated in the preferred form that the source 10 will provide a frequency of radiation to which the photodetector 14 is sensitive and which will be substantially absent from background radiation.

When the output of the differential amplifier 20 decreases to a predetermined level, formation of condensation on the mirror 1 is indicated. The output of the differential amplifier 20 is connected to a prior art temperature sensing circuit 22 receiving an output from the temperature sensitive resistance 4. The temperature signal indicative of dew point is provided by the temperature sensing circuit 22. The output of the differential amplifier 20 is also connected in a prior art manner to a thermoelectric cooler servo amplifier and temperature control circuit 24 having an output connected to the thermoelectric cooler 3 to modulate the current thereto to maintain a substantially constant condensation thickness on the mirror 1.

Additionally, in accordance with the present invention, the photosensors are connected to provide a common mode, i.e. additive, output to a summing amplifier. The common mode output provides a signal indicative of the sums of the reflected and scattered radiation emitted by the source 10. Assuming the mirror 1 does not have other factors influencing a reduction in reflectivity from the source 1 to the photodetector, the teen, the sum of the outputs of the photosensors 13 and 14 will be indicative of the performance of the system in terms of providing reflectivity. In the total absence of condensation or incomplete covering of the mirror 1 with condensation, total outputs of the photosensors 13 and 14 will remain within a predetermined range. With the formation of dirt on the mirror, the output of the summing amplifier 30 will decrease. For purposes of the present invention, this operation is referred to as measuring the reflectivity of the mirror 1.

In various embodiments, the output of the summing amplifier 30 may be utilized in one or all of the following ways. The output of the amplifier 30 may be connected to a threshold sensing amplifier 31 providing an output to utilization means 33.

The utilization means 33 may comprise a light emitting diode. When the input to the amplifier 31 decreases below a predetermined level, a total reflectivity of the mirror 1 below a selected is indicated and the light emitting diode 33 is operated to comprise a signal associated with a message, e.g. "clean mirror", to inform an operator that cleaning of the mirror is necessary. The output of the amplifier 31 may be further connected to the temperature control circuit 24 to initiate a prior art heating and cooling cycle. It is known in the prior art as a means of removing reflection-reducing material from a mirror to heat the mirror above the dew point whereupon certain solid material, or other inteferring substance, to a degree is removed with the condensation. Total reflectivity of the mirror 1 while reduced will still remain within usable limits.

The output of the summing amplifier 30 is further connected to a servo amplifier 36 to maintain the output signal delivered to the summing amplifier 30 within preselected limits by providing an input to a control circuit 37 having an output connected to the source 10. When total reflectivity decreases below a selected level, the circuit operates in a closed loop manner to increase the intensity of the source 10 to maintain the output of the amplifier 30 within available limits based upon component selection. Consequently, even when total reflectivity of the mirror 1 is reduced below what would be an acceptable level in a circuit in which intensity of the source 10 could not be modulated, acceptable operation may still be provided. Consequently, time between necessity for cleaning operations is maximized.

Downtime is minimized. What is thus provided is an improved system in which cleaning operations are initiated in response to system performance rather than in response to a schedule or a total loss of performance. Furthermore, system performance may be monitored continuously without interrupting moisture sensing operation. The disclosure herein is written with a view toward enabling those skilled in the art to provide many different embodiments, all of which may be constructed in accordance with the present invention.

What is claimed is new and desired to be secured by Letters Patent of the United States is:

1. In a chilled mirror hygrometer comprising a radiation source, means for reflecting radiation from said source, thermoelectric means regulating the temperature of said reflecting means for alternately forming and evaporating condensation on said reflecting means, first photodetector means for providing a first d.c. signal indicative of radiation from said source in the absence of condensation on said reflecting means, second photodetector means for providing a second d.c. signal indicative of radiation from said source scattered by condensation on said reflecting means, the improvement comprising means responsive to the in phase sum of said d.c. signals from said first and second photodetectors means for providing an output signal indicative of reflectivity of said reflecting means, whereby reflectivity of the reflecting means may be sensed during operation of said chilled mirror hygrometer.

2. The improvement according to claim 1 wherein said first and second photodetectors means comprise phototransistors and said means for providing an output signal comprise means for providing a common mode signal from said first and second phototransistors.

3. The improvement according to claim 2 further comprising comparison means for comparing said output signal to a preselected threshold level and operating utilization means to a first or second state in response to said comparison.

4. The improvement according to claim 3 wherein said utilization means comprises display means for selectively indicating a message that reflectivity of said reflecting means is within preselected limits.

5. The improvement according to claim 3 wherein said utilization means comprises threshold responsive means for initiating a heating cycle wherein the output of said utilization means is connected to control means for said thermo electric means.

6. Apparatus according to claim 3 wherein said utilization means comprises means for controlling the intensity of said radiation source in response to indication of reflectivity of said reflectivity means.

* * * * *